United States Patent
Liu et al.

(10) Patent No.: US 12,221,632 B2
(45) Date of Patent: Feb. 11, 2025

(54) VIRUS LYSIS AND NUCLEIC ACID PRESERVATION SOLUTION

(71) Applicant: GUANGZHOU DONGSHENG BIOTECH CO., LTD., Guangzhou (CN)

(72) Inventors: Yuandong Liu, Guangzhou (CN); Wei Meng, Guangzhou (CN); Meiying Chen, Guangzhou (CN); Qin Huang, Guangzhou (CN); Qingqing Chen, Guangzhou (CN); Ning Zhou, Guangzhou (CN)

(73) Assignee: GUANGZHOU DONGSHENG BIOTECH CO., LTD., Guangzhou (CN)

( * ) Notice: Subject to any disclaimer, the term of this patent is extended or adjusted under 35 U.S.C. 154(b) by 725 days.

(21) Appl. No.: 17/389,371

(22) Filed: Jul. 30, 2021

(65) Prior Publication Data

US 2022/0017874 A1    Jan. 20, 2022

Related U.S. Application Data

(63) Continuation of application No. PCT/CN2021/074681, filed on Feb. 1, 2021.

(30) Foreign Application Priority Data

Jun. 22, 2020   (CN) .......................... 202010571607.0

(51) Int. Cl.
*C12N 7/00*     (2006.01)
*C12N 15/10*    (2006.01)

(52) U.S. Cl.
CPC ........... *C12N 7/00* (2013.01); *C12N 15/1013* (2013.01)

(58) Field of Classification Search
CPC .............................. C12N 7/00; C12N 15/1013
See application file for complete search history.

(56) References Cited

U.S. PATENT DOCUMENTS

| | | | | |
|---|---|---|---|---|
| 9,999,217 B2 * | 6/2018 | Whitney | ............. | C12Q 1/6806 |
| 10,174,362 B2 * | 1/2019 | Gaeta | .................. | C12Q 1/6806 |
| 2014/0065627 A1 * | 3/2014 | Whitney | ............. | C12Q 1/6806 |
| | | | | 435/6.12 |

FOREIGN PATENT DOCUMENTS

| | | | | |
|---|---|---|---|---|
| CN | 106906207 A | 6/2017 | | |
| CN | 109207476 A | 1/2019 | | |
| CN | 109971749 A | 7/2019 | | |
| CN | 111172239 A | 5/2020 | | |
| CN | 111235145 A | * | 6/2020 | |
| CN | 111304175 A | * | 6/2020 | ............... C12N 7/00 |
| CN | 111690640 A | 9/2020 | | |

OTHER PUBLICATIONS

Tris-HCI Buffer Recipe. Cold Spring Harbor Protocol (2006). doi:10.1101/pdb.rec8747 (Year: 2006).*
Scallan et al (Apr. 13, 2020). Validation of a Lysis Buffer Containing 4 M Guanidinium Thiocyanate (GITC)/ Triton X-100 for Extraction of SARS-COV-2 RNA for COVID-19 . . . Lysis Buffers Containing 4 to 6 M GITC, Roche External Lysis Buffer and Qiagen RTL Lysis Buffer. bioRxi (Year: 2020).*
Li et al (2018). Current status on the development of pseudoviruses for enveloped viruses. Rev Med Virol. 2018;28:e1963. (Year: 2018).*
Zhao et al (Feb. 27, 2020). A simple magnetic nanoparticles-based viral RNA extraction method for efficient detection of SARS-CoV-2. bioRxiv (2020) pp. 1-18. (Year: 2020).*
J. Sambrook, et al., Molecular Cloning: A Laboratory Manual, pp. 936-939, China Science Press Co., Ltd.

* cited by examiner

*Primary Examiner* — Nicole Kinsey White
*Assistant Examiner* — Samadhan Jaising Jadhao
(74) *Attorney, Agent, or Firm* — Bayramoglu Law Offices LLC

(57) ABSTRACT

A virus lysis and nucleic acid preservation solution is disclosed, including the following components: isopropanol or ethyl alcohol, guanidinium chloride, tri (hydroxymethyl) aminomethane hydrochloride, and ethylenediaminetetraacetic acid. Furthermore, a kit including the virus lysis and nucleic acid preservation solution, a method for preserving viral nucleic acid, and a method for extracting a viral nucleic acid are also provided. The virus lysis and nucleic acid preservation solution of the present invention has the functions of lysing virus and preserving nucleic acid in the lysed virus samples, and it is compatible with lysis buffers, wash buffers, elution buffers, etc. in all kinds of viral nucleic acid extraction kit commonly available in the market.

13 Claims, 9 Drawing Sheets

Specification includes a Sequence Listing.

VIRUS LYSIS AND NUCLEIC ACID PRESERVATION SOLUTION

CROSS REFERENCE TO THE RELATED APPLICATIONS

This application is a continuation application of International Application No. PCT/CN2021/074681, filed on Feb. 1, 2021, which is based upon and claims priority to Chinese Patent Application No. 202010571607.0, filed on Jun. 22, 2020, the entire contents of which are incorporated herein by reference.

SEQUENCE LISTING

The instant application contains a Sequence Listing which has been submitted in ASCII format via EFS-Web and is hereby incorporated by reference in its entirety. Said ASCII copy is named GBXYY001-PKG_Sequence Listing.txt, created on Jul. 15, 2021 and is 1,761 bytes in size.

TECHNICAL FIELD

The present invention belongs to the technical field of biomedicine, and specifically relates to a virus preservation solution, a kit, a method for preserving a virus, and a method for extracting a viral nucleic acid.

BACKGROUND

In modern medical laboratory science, the detection of pathogenic viruses relies on the nucleic acids (DNA, RNA) extracted from suspected samples. Due to time or space limitations, a sample to be tested generally needs to be preserved for a period of time or sent to a specific place for detection.

Currently, virus preservation solutions available on the market, such as Hanks' solution and phosphate-buffered saline (PBS) solution, can meet the above needs. However, there are still some drawbacks. The virus content is relatively low in many samples, after the sample is diluted with about 3 mL of preservation solution, only a maximum of 200 μL of the sample-containing preservation solution is taken for lysis using lysis buffer and then subjected to nucleic acid extraction, resulting in extremely low amount of extracted nucleic acid. In addition, traditional virus preservation solutions can only preserve samples for a short time at low temperature.

At present, the mainstream magnetic bead-based viral nucleic acid extraction kits are composed of proteinase K and lysis buffer, such as those from TIANGEN Biotech (Beijing) Co., Ltd, Vazyme Biotech Co., Ltd., Beaver Biosciences Inc., Guangzhou Magen Biotechnology Co., Ltd., etc. Under the condition of high concentration of ionizing agent, silicon-based magnetic particles can adsorb nucleic acid through hydrogen bonding and electrostatic interaction, while proteins or other impurities are not adsorbed and thus removed. The nucleic acid-adsorbed nanoparticles are washed to remove proteins and salts, and finally the nucleic acids on the magnetic beads can be eluted with a low-salt buffer (such as TE Buffer) or water. The kit can only extract a relatively small amount of sample, with a standard loading of 200 μL. The reason is that conventional virus preservation is performed using Hanks' solution or PBS, and increasing the sample amount will reduce the salt concentration of lysis buffer, resulting in a decrease in the yield of nucleic acid. At the same time, when the sample amount is less than 200 μL, PBS is required to be used as supplement, which also leads to a low yield of nucleic acid. Patent Application No. 202010128653.3 discloses a guanidine thiocyanate-based sample preservation solution. However, such guanidine thiocyanate-containing sample preservation solution may lead to the inactivation of protease K in nucleic acid extraction reagents and the aggregation of magnetic beads, which will eventually result in a decline in nucleic acid yield.

Therefore, it is quite necessary to develop a virus preservation solution that can effectively preserve and lysing virus samples and is compatible with common viral nucleic acid extraction kits on the market.

SUMMARY

In view of this, the purpose of the present invention is to provide a virus preservation solution that has preservation and lysis abilities, can be stored and transported at room temperature, and is highly safe and compatible with various magnetic bead-based viral nucleic acid extraction kits.

To solve the above problem, the virus preservation solution of the present invention includes: guanidine hydrochloride, tris (hydroxymethyl) aminomethane hydrochloride, ethylenediaminetetraacetic acid, and isopropanol or ethyl alcohol.

In the virus preservation solution of the present invention, preferably, a concentration of the guanidine hydrochloride is 2-6 mol/L, a concentration of the tris (hydroxymethyl) aminomethane hydrochloride is 10-100 mmol/L, a concentration of the ethylenediaminetetraacetic acid is 2-5 mmol/L, and a volume percentage of the isopropanol or ethyl alcohol is 5%-40%.

In the virus preservation solution of the present invention, further preferably, the concentration of the guanidine hydrochloride is 3-5 mol/L, the concentration of the tris (hydroxymethyl) aminomethane hydrochloride is 50-80 mmol/L, the concentration of the ethylenediaminetetraacetic acid is 2.5-4 mmol/L, and the volume percentage of the isopropanol or ethyl alcohol is 10%-30%.

A pH value of the virus preservation solution of the present invention is 6-9, preferably 7-8.

The virus preservation solution of the present invention is prepared by using sterile water as a solvent, and a preparation method thereof specifically includes: adding the guanidine hydrochloride, the tris (hydroxymethyl) aminomethane hydrochloride, the ethylenediaminetetraacetic acid, the isopropanol or ethyl alcohol into the sterile water, and mixing well with stirring.

The guanidine hydrochloride in the virus preservation solution of the present invention is a protein denaturing agent, which can dissolve proteins, destroy cell structures, and dissociate nucleoproteins into nucleic acids, thus a reduced amount of or even no lysis buffer is needed in subsequent nucleic acid extraction. In addition, the guanidine hydrochloride can inactivate RNA enzyme to avoid RNA degradation. The tris (hydroxymethyl) aminomethane hydrochloride is a commonly used buffer reagent, which can concurrently maintain the stability of the preservation solution and the stability of the nucleic acids. The ethylenediaminetetraacetic acid is a commonly used metal ion chelator, which can inhibit the activity of nuclease and help to maintain the stability of the nucleic acids. The isopropanol or ethyl alcohol precipitates and enriches the nucleic acids, which is beneficial to the subsequent nucleic acid extraction.

The virus preservation solution of the present invention has a conventional concentration, and can be used to preserve virus samples collected from nasal cavity, oral cavity, throat and other parts or other samples that may contain viruses including pseudoviruses. The genetic material of these viruses is deoxyribonucleic acid (DNA) or ribonucleic acid (RNA).

A method of extracting viral nucleic acids from a sample preserved in the virus preservation solution of the present invention includes using a magnetic bead-based nucleic acid extraction kit to perform a nucleic acid extraction on the sample preserved in the virus preservation solution. The sample preserved in the virus preservation solution can be mixed with the lysis buffer at any proportion ranging from the proportion recommended by the magnetic bead-based viral nucleic acid extraction kit to 100% (i.e., without the use of the lysis buffer) for performing follow-up extraction operations.

The common amount of the sample and the lysis buffer recommended by the magnetic bead-based viral nucleic acid extraction kit is 400 μl or 500 μL of the lysis buffer per 200 μL of the sample-containing virus preservation solution (using PBS solution or normal saline as supplement when less than 200 μL), that is, the sample generally accounts for 50% or less of the used lysis buffer. When a magnetic bead-based nucleic acid extraction is performed, the use amount of the sample preserved in the virus preservation solution of the present invention can be increased to 100% without using the lysis buffer, which is conducive to improving the yield of nucleic acid. The magnetic bead-based nucleic acid extraction kit is not specifically limited, can contain proteinase K, and is compatible with the virus preservation solution of the present invention. Moreover, the guanidine hydrochloride in the virus preservation solution will not cause proteinase K inactivation or aggregation of magnetic beads, thus not reducing the yield of nucleic acids. Magnetic bead-based methods include manual nucleic acid extraction methods and automated nucleic acid extraction methods. Magnetic beads refer to bio-magnetic beads used for nucleic acid purification, including but not limited to hydroxyl magnetic beads and carboxyl magnetic beads. Lysis buffer is a solution capable of lysing the virus sample and releasing nucleic acid, either commercially available (including those included in the nucleic acid extraction kit) or a solution disclosed in a literature.

According to the embodiments of the present invention, the virus preservation solution of the present invention is of inactivated type, which has the function of preserving and lysing virus samples, and can be compatible with various types of magnetic bead-based viral nucleic acid extraction kits commonly available in the market. When nucleic acid is extracted, the sample and the lysis buffer can be mixed at any proportion ranging from the proportion recommend by the kit to 100%, that is, a reduced amount of or even no lysis buffer is needed, thus increasing the amount of the sample and obtaining more viral nucleic acids and more accurate detection results. The virus preservation solution of the present invention has simple components, is convenient for raw material availability, and has low cost. Moreover, the virus preservation solution can preserve samples at room temperature for a long time, and does not need to be inactivated at high temperature inactivation, which is very safe for operating personnel and environment, at the same time, reduces the possibility of RNA degradation, thus obtaining more nucleic acids, and reducing the rate of missed detection.

Compared with the traditional virus preservation solution, the virus preservation solution of the present invention has the following advantages:

1. The virus preservation solution of the present invention has the functions of preserving and lysing virus samples, and it is compatible with lysis buffers, wash buffers, elution buffers, etc. in all kinds of viral nucleic acid extraction kit commonly available in the market, regardless of the specific components therein, such as proteinase K, etc. Since the virus preservation solution has the lysis function, the sample and lysis buffer can be mixed at any proportion ranging from the proportion recommended by the magnetic bead-based viral nucleic acid extraction kit to 100% when performing follow-up extraction, that is, a reduced amount of or even no lysis buffer is needed, thus increasing the amount of the sample used. In this way, the amount of the sample used is increased at least by three times, so as to obtain more viral nucleic acids and more accurate detection results.

2. The virus preservation solution of the invention has simple components, is convenient for raw material availability and preparation, and has low cost. Moreover, the virus preservation solution can preserve samples at room temperature for a long time. The samples can be stably preserved at 15-25° C. for at least 6 days, which is conducive to long-time or long-distance transportation, and reduces the possibility of nucleic acid degradation due to improper transport or storage. Moreover, it solves the problem that traditional virus preservation solutions can only preserve samples for a short period at low temperature.

3. The virus preservation solution of the present invention is an inactivated virus preservation solution that can inactivate viruses, which is very safe for operating personnel and environment, and can also avoid RNA degradation. Samples stored in non-inactivated virus preservation solution require to be inactivated at high temperature before nucleic acid extraction, while the high temperature inactivation may lead to RNA degradation and thereby result in a false negative nucleic acid testing result. The high-temperature inactivation procedure is not required when using the virus preservation solution of the present invention, thus simplifying the operation process, and reducing the possibility of contamination. Meanwhile, it has the effects of inhibiting RNA enzyme activity, reducing the possibility of RNA degradation, and reducing artificial damage to the nucleic acid sample, thus obtaining more nucleic acids and reducing the rate of missed detection. Additional aspects and advantages of the present invention will be partially given in the following description, and will become apparent therefrom, or be known through the practice of the present invention.

BRIEF DESCRIPTION OF THE DRAWINGS

The foregoing and/or additional aspects and advantages of the present invention will become apparent and easy to understand from the description of the embodiments in conjunction with the following drawings, specifically.

DETAILED DESCRIPTION OF THE EMBODIMENTS

Figure 1:
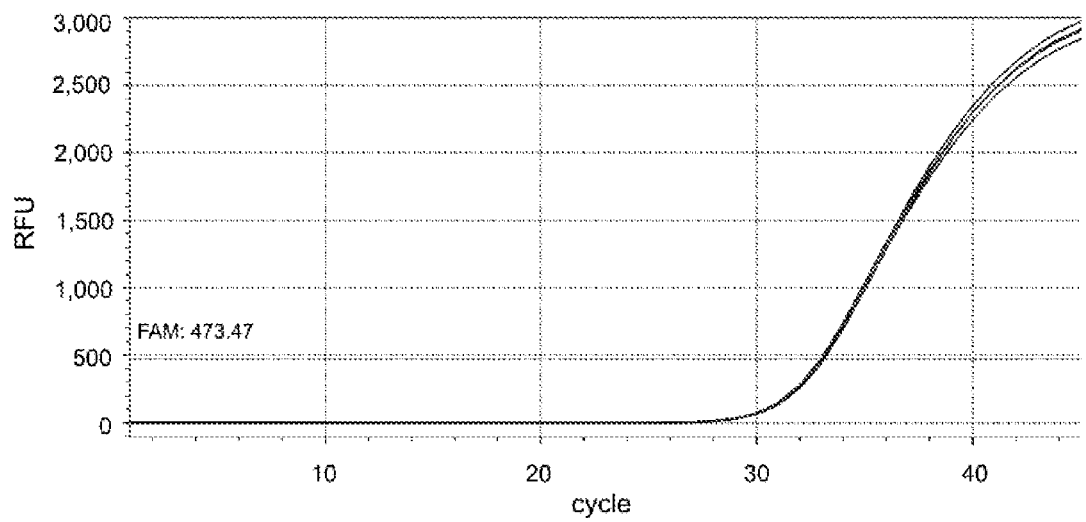
FIG. 1 shows a stability test result of the sample-containing virus preservation solution placed at room temperature for 2 days.

The embodiments of the present invention are described in detail below with reference to the drawings. The embodiments described below with reference to the accompanying drawings are exemplary and are intended to explain the present invention rather than limiting the present invention.

Term Explanation

Unless otherwise specified, the "first", "second", "third" and other similar terms used in this invention are used for the convenience of description and for distinguishing purposes, and do not imply or express any order or significance difference for any purpose. Meanwhile, it does not mean that the content defined by "first", "second", "third" and other similar terms consists of only one component.

The solution of the present invention will be explained below in conjunction with embodiments. Those skilled in the art will understand that the following embodiments are only used to illustrate the present invention, and should not be regarded as limiting the scope of the present invention. Those without indication of specific techniques or conditions in the embodiments follow the techniques or conditions described in the literature in the field (for example, refer to the J. Sambrook et al., "Molecular Cloning: A Laboratory Manual", which is translated by J Huang Peitang et al., third edition, Science Press) or follow the product manual. The reagents or instruments used without the identification of manufacturer are all conventional products that can be purchased commercially, for example, they can be purchased from Illumina, Inc.

Embodiment 1: Preparation of Virus Preservation Solution

Guanidine hydrochloride, tris (hydroxymethyl) aminomethane hydrochloride, ethylenediaminetetraacetic acid and isopropanol were added into 1000 mL of sterile water, followed by stirring and mixing evenly to obtain the virus preservation solution. The concentration of the guanidine hydrochloride was 5 mol/L, the concentration of the tris (hydroxymethyl) aminomethane hydrochloride was 60 mmol/L, the concentration of the ethylenediaminetetraacetic acid was 3 mmol/L, the volume percentage of the isopropanol was 20%, and the pH of the virus preservation solution was 8.

Embodiment 2: Preparation of Virus Preservation Solution

Guanidine hydrochloride, tris (hydroxymethyl) aminomethane hydrochloride, ethylenediaminetetraacetic acid and isopropanol were added into 1000 mL of sterile water, followed by stirring and mixing evenly to obtain the virus preservation solution. The concentration of the guanidine hydrochloride was 4 mol/L, the concentration of the tris (hydroxymethyl) aminomethane hydrochloride was 80 mmol/L, the concentration of the ethylenediaminetetraacetic acid was 4 mmol/L, the volume percentage of the isopropanol was 30%, and the pH of the virus preservation solution was 7.5.

Embodiment 3: Preparation of Virus Preservation Solution

Guanidine hydrochloride, tris (hydroxymethyl) aminomethane hydrochloride, ethylenediaminetetraacetic acid and isopropanol were added into 1000 mL of sterile water, followed by stirring and mixing evenly to obtain the virus preservation solution. The concentration of the guanidine hydrochloride was 3 mol/L, the concentration of the tris (hydroxymethyl) aminomethane hydrochloride was 50 mmol/L, the concentration of the ethylenediaminetetraacetic acid was 2.5 mmol/L, the volume percentage of the isopropanol was 10%, and the pH of the virus preservation solution was 7.

Embodiment 4: Preparation of Virus Preservation Solution

Guanidine hydrochloride, tris (hydroxymethyl) aminomethane hydrochloride, ethylenediaminetetraacetic acid and isopropanol were added into 1000 mL of sterile water, followed by stirring and mixing evenly to obtain the virus preservation solution. The concentration of the guanidine hydrochloride was 2 mol/L, the concentration of the tris (hydroxymethyl) aminomethane hydrochloride was 10 mmol/L, the concentration of the ethylenediaminetetraacetic acid was 2 mmol/L, the volume percentage of the isopropanol was 5%, and the pH of the virus preservation solution was 6.

Embodiment 5: Preparation of Virus Preservation Solution

Guanidine hydrochloride, tris (hydroxymethyl) aminomethane hydrochloride, ethylenediaminetetraacetic acid and isopropanol were added into 1000 mL of sterile water, followed by stirring and mixing evenly to obtain the virus preservation solution. The concentration of the guanidine hydrochloride was 6 mol/L, the concentration of the tris (hydroxymethyl) aminomethane hydrochloride was 100 mmol/L, the concentration of the ethylenediaminetetraacetic acid was 5 mmol/L, the volume percentage of the isopropanol was 40%, and the pH of the virus preservation solution was 9.

In order to show the advantages of the present invention, various tests were carried out by the inventors using the virus preservation solutions of the above embodiments. The virus preservation solution of Embodiment 1 was used for tests 1-6, and the virus preservation solution of Embodiment 3 was used for test 7. The specific tests were as follows.

Test 1. Stability Test of Virus Samples Preserved in Virus Preservation Solution Samples of test group: 2 μL of pseudoviruses ($1 \times 10^4$ copies/mL, simulating severe acute respiratory syndrome coronavirus 2 (SARS-CoV-2), single-strand RNA virus, similarly hereinafter) were mixed with 198 μL of human saliva to simulate a saliva sample, which was then added into 600 μL of virus preservation solution and placed at room temperature (25° C.) for 2, 4 and 6 days, respectively.

Samples of control group: before the experiment, 2 μL of pseudovirus (stored at −20° C., $1 \times 10^4$ copies/mL) was taken and immediately mixed with 198 μL of human saliva and added into 600 μL of virus preservation solution.

The magnetic bead-based viral nucleic acid extraction kit (Dongsheng V4002) was used for automated nucleic acid extraction. 20 μL of magnetic beads, 2 μL of carrier RNA, and 20 μL of proteinase K were added to the samples of test group and the samples of control group, respectively. After mixing well, the samples were transferred to well 1 (referring to the first column) of the 96-well deep-well plate. Wash buffer, wash buffer and elution buffer were respectively added in well 2, well 3 and well 4 of the 96-well deep-well plate for nucleic acid extraction. The 96-well deep-well plate was installed in the correct position of the automated nucleic acid extraction instrument (Auto-Pure32A, Hangzhou Allsheng Instruments Co., Ltd.), and the nucleic acid extraction was carried out according to the procedure in Table 1.

TABLE 1

Nucleic acid extraction procedures

| Step | Well | Name | Mixing time | Magnetic adsorption time | Latency time | Volume | Mixing speed | Temperature |
|---|---|---|---|---|---|---|---|---|
| 1 | 1 | Lysis | 10 min | 0 | 2 min | 840 μL | 8 level | OFF |
| 2 | 1 | Magnetic adsorption | 0 | 90 sec | 0 | 840 μL | 8 level | OFF |
| 3 | 2 | Wash 1 | 2 min | 60 sec | 0 | 600 μL | 8 level | OFF |
| 4 | 3 | Wash 2 | 2 min | 60 sec | 2 min | 600 μL | 8 level | OFF |
| 5 | 4 | Elution | 3 min | 60 sec | 0 | 50 μL | 8 level | OFF |
| 6 | 1 | Drop | 0.5 min | 0 | 0 | 840 μL | 8 level | OFF |

After extraction, the nucleic acid samples were obtained. One-step RT-qPCR Kit (Guangzhou Dongsheng V5001) was used to complete RNA reverse transcription and quantitative fluorescence PCR (qPCR), and the RT-qPCR reaction solution was prepared according to the system in Table 2.

TABLE 2

RT-qPCR Reaction solution system

| Reagent | Dosage | Final concentration |
|---|---|---|
| 2 × One-step U+ Mix | 15 μL | 1× |
| One-step U+ Enzyme Mix | 1.5 μL | — |
| Forward primer (10 μM) | 0.6 μL | 0.2 μM |
| Reverse primer (10 μM) | 0.6 μL | 0.2 μM |
| Fluorescent probe (10 μM) | 0.3 μL | 0.1 μM |
| Template RNA | 1 pg-1 μg | 1 pg-1 μg/30 μL |
| RNase-free ddH$_2$O | Fill up to 300 μL | — |

The primers and the fluorescent probe used in Table 2 are recommended by the Chinese Center for Disease Control and Prevention (CDC) for the detection of coronavirus target gene ORF1Ab. The specific sequences are as follows:

```
Forward primer:
                                   (SEQ ID NO: 1)
CCCTGTGGGTTTTACACTTAA Reverse primer:
                                   (SEQ ID NO: 2)
ACGATTGTGCATCAGCTGA Fluorescent probe:
                                   (SEQ ID NO: 3)
5'-FAM-CCGTCTGCGGTATGTGGAAAGGTTATGG-BHQ1-3'
```

The RT-qPCR reaction solution was placed on a real-time quantitative fluorescence PCR instrument (Xi'an Tianlong, TL988) for nucleic acid quantitative detection, with two repeats in each group. The reaction procedure was shown in Table 3.

TABLE 3

RT-qPCR reaction procedure

| Reverse transcription | 55° C. | 15 min | / |
|---|---|---|---|
| Initial denaturation | 95° C. | 30 sec | / |
| Cyclic reaction | 95° C. | 10 sec | 45 Cycles |
| | 60° C. | 30 sec | |

Figure 2:
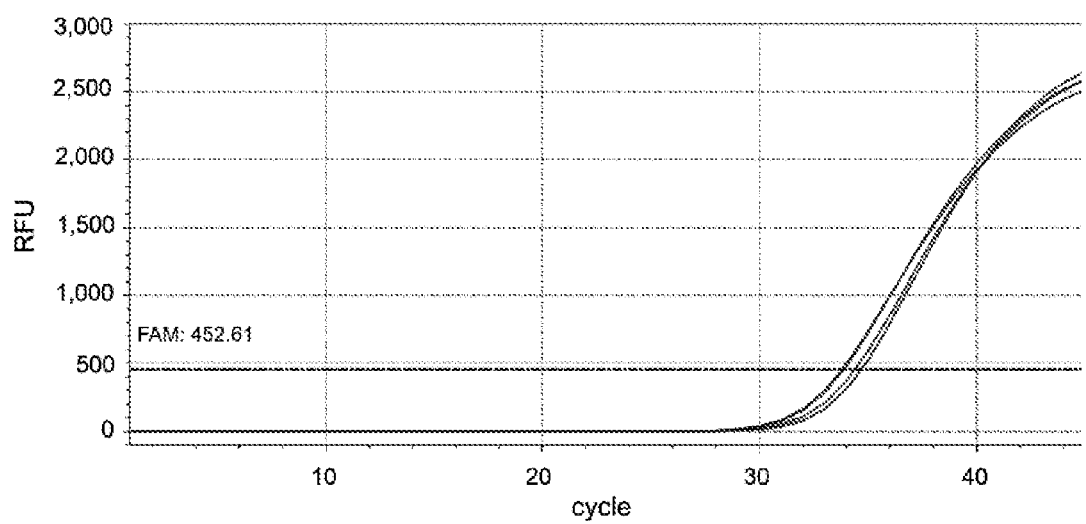
FIG. 2 shows a stability test result of the sample-containing virus preservation solution placed at room temperature for 4 days.
Figure 3:
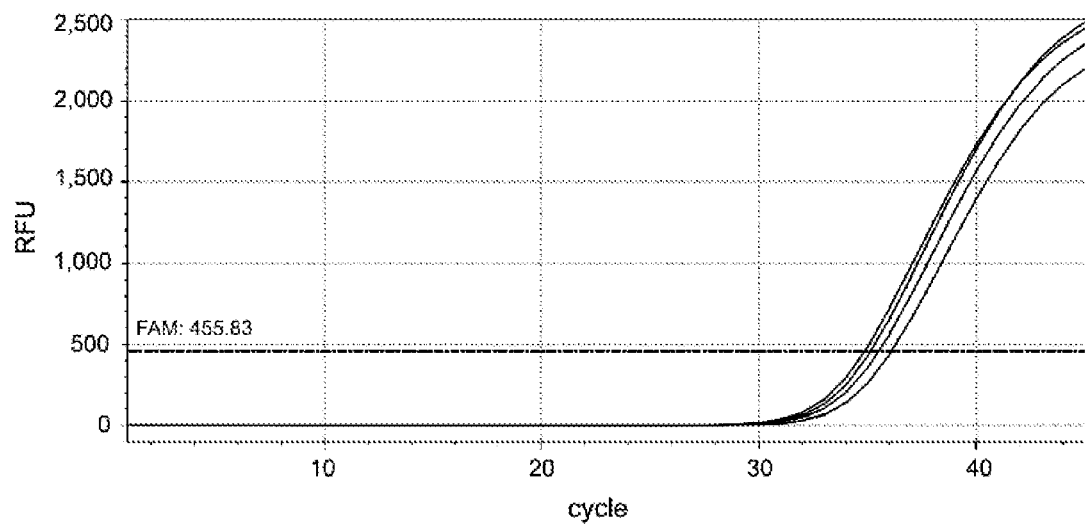
FIG. 3 shows a stability test result of the sample-containing virus preservation solution placed at room temperature for 6 days.

The nucleic acid testing results of the samples of test group stored at room temperature for 2, 4 and 6 days were shown in FIGS. 1-3, and the corresponding Ct values were shown in Table 4.

TABLE 4

Ct values of test group and control group after being placed for 2, 4 and 6 days at room temperature

| Time of samples to be placed | Ct values of test group | Ct values of control group | Average Ct value |
| --- | --- | --- | --- |
| 2 days | 33.12 | 33.03 | 0.06 |
|  | 32.95 | 32.96 |  |
| 4 days | 33.79 | 34.39 | −0.70 |
|  | 33.88 | 34.69 |  |
| 6 days | 35.12 | 35.51 | −0.81 |
|  | 34.86 | 36.09 |  |

FIGS. 1-3 showed that, with the increase of the time that the samples were placed at room temperature, the pseudoviruses having a low concentration were degraded slowly in the virus preservation solution and could still be detected after being placed for 6 days. As can be seen from Table 4, there was no significant difference between the Ct values of the test group and the control group, or the Ct values of the test group were smaller, indicating that the virus preservation solution of the present invention can preserve the virus samples at room temperature for at least 6 days, and shows better preservation effect than that stored at −20° C. without virus preservation solution.

Test 2. Test of Virus Preservation Solution Replacing Lysis Buffer

Preservation solution A: 10 µL of pseudoviruses (1×10⁴ copies/mL) and a nasopharyngeal swab sample were added together into 3 mL of virus preservation solution and placed at room temperature (25° C.) for 2 h.

Automated nucleic acid extraction was performed using the magnetic bead-based viral nucleic acid extraction kit (Dongsheng V4002):

Test group: 800 µL of the preservation solution A was added to the following reagents: 20 µL of magnetic beads, 2 µL of carrier RNA, and 20 µL of proteinase K, followed by mixing well and transferring to well 1 of a 96-well deep-well plate.

Control group: 200 µL of the preservation solution A was added to the following reagents: 20 µL of magnetic beads, 2 µL of carrier RNA, 20 µL of proteinase K, and 600 µL of lysis buffer, followed by mixing well and transferring to well 1 of a 96-well deep-well plate.

The subsequent extraction operation was the same as that in test 1. After extraction, the nucleic acid samples were obtained. The nucleic acid detection procedure was the same as that in test 1. The primers and fluorescent probe used for nucleic acid detection were recommended by the Chinese Center for Disease Control and Prevention (CDC) for the detection of coronavirus target gene N. The specific sequences were as follows:

```
Forward primer:
                                          (SEQ ID NO: 4)
GGGGAACTTCTCCTGCTAGAAT Reverse primer:
                                          (SEQ ID NO: 5)
CAGACATTTTGCTCTCAAGCTG Fluorescent probe:
                                          (SEQ ID NO: 6)
5'-HEX-TTGCTGCTGCTTGACAGAT-TAMRA-3'
```

(the fluorescent group was changed from the recommended FAM to HEX, which did not affect the judgment of test results)

Figure 4:
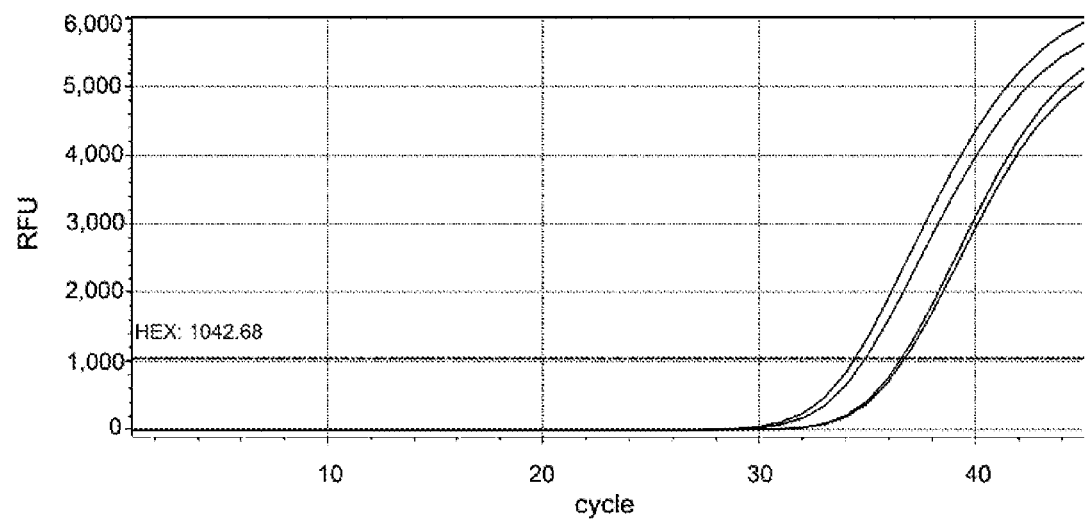
FIG. 4 shows an extraction effect of a sample lysed directly with the virus preservation solution without the addition of lysis buffer.

The nucleic acid testing results were shown in FIG. 4, and the corresponding Ct values were shown in Table 5.

TABLE 5

Ct values of test group and control group

| Sample | Ct values | Average Ct value |
| --- | --- | --- |
| Test group | 34.92 | 34.68 |
|  | 34.44 |  |
| Control group | 36.75 | 36.68 |
|  | 36.61 |  |

As can be seen from FIG. 4 and Table 5, the Ct value of the test group was about 2 less than that of the control group, indicating that more nucleic acids can be extracted when the virus preservation solution of the present invention completely replaced the lysis buffer.

Test 3. Compatibility Test of Virus Preservation Solution and Lysis Buffer Mixed at Different Ratios Preservation solution B: 10 µL of pseudoviruses (1×10⁵ copies/mL) and a nasopharyngeal swab sample were added together into 3 mL of virus preservation solution. A blank control (B0) without the sample was prepared.

Preservation solution C: 10 µL of pseudoviruses (1×10⁵ copies/mL) and a nasopharyngeal swab sample were added together into 3 mL of phosphate buffer (PBS, 0.01 M). A blank control (C0) without samples was prepared.

After being placed at room temperature (25° C.) for 1 h, automated nucleic acid extraction was performed by using the magnetic bead-based viral nucleic acid extraction kit (Dongsheng V4002). The preservation solution and lysis buffer were mixed according to the volume ratio in Table 6. The blank controls B0 and C0 were not added with lysis buffer.

TABLE 6

Volume ratio of mixed preservation solution and lysate solution

| Preservation solution/lysis buffer | Preservation solution (µL) | lysis buffer (µL) |
| --- | --- | --- |
| 1/7 | 100 | 700 |
| 1/3 | 200 | 600 |
| 1/1 | 400 | 400 |
| 8/0 | 800 | 0 |

20 µL of magnetic beads, 2 µL of carrier RNA, and 20 µL of proteinase K were added to the above solutions, respectively, followed by mixing well and transferring to 96-well deep-well plates. The subsequent extraction operation was the same as that in test 1. The nucleic acid samples were obtained after extraction. The nucleic acid detection procedure was the same as that in test 1. The nucleic acid testing results were shown in FIG. 5 and FIG. 7, and the corresponding Ct values were shown in Table 7.

TABLE 7

Ct values of test group and control group

| Sample | Ct values | Average Ct value |
|---|---|---|
| B1/7 | 32.40 | 32.26 |
|  | 32.11 |  |
| B1/3 | 29.59 | 29.69 |
|  | 29.79 |  |
| B1/1 | 28.68 | 28.71 |
|  | 28.74 |  |
| B8/0 | 27.76 | 27.75 |
|  | 27.73 |  |
| B0 | — | — |
|  | — |  |
| C1/7 | 34.68 | 35.32 |
|  | 35.96 |  |
| C1/3 | 32.96 | 32.89 |
|  | 32.82 |  |
| C1/1 | 31.46 | 31.41 |
|  | 31.36 |  |
| C8/0 | 29.82 | 29.80 |
|  | 29.77 |  |
| C0 | — | — |
|  | — |  |
| No template control (NTC) | — | — |
|  | — |  |

Figure 5:
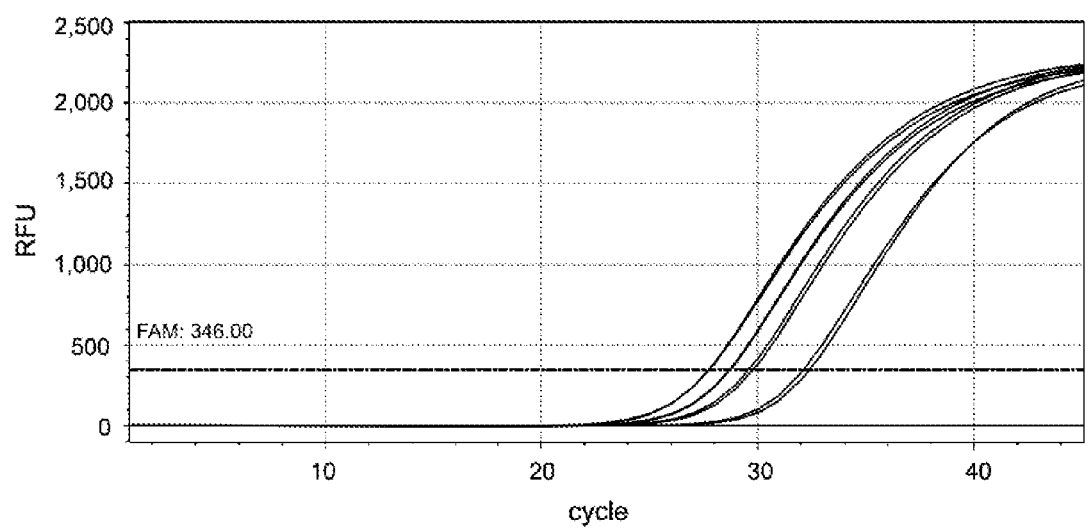
FIG. 5 shows a compatibility test of the virus preservation solution of Embodiment 1 and lysis buffer mixed at different ratios.
Figure 6:
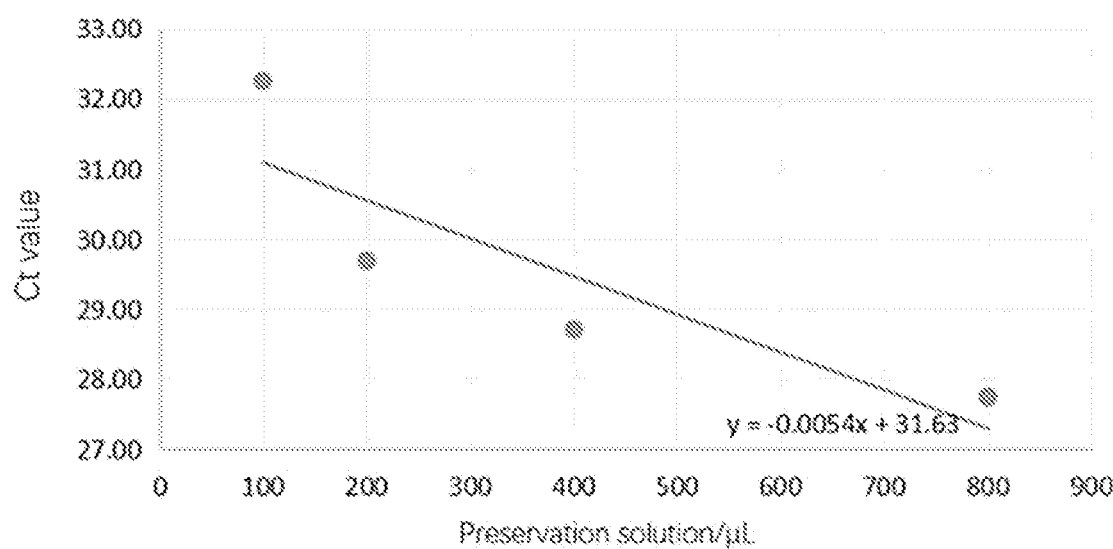
FIG. 6 shows a change trend of cycle threshold (Ct) value during the compatibility test of the virus preservation solution of Embodiment 1 and lysis buffer mixed at different ratios.
Figure 7:
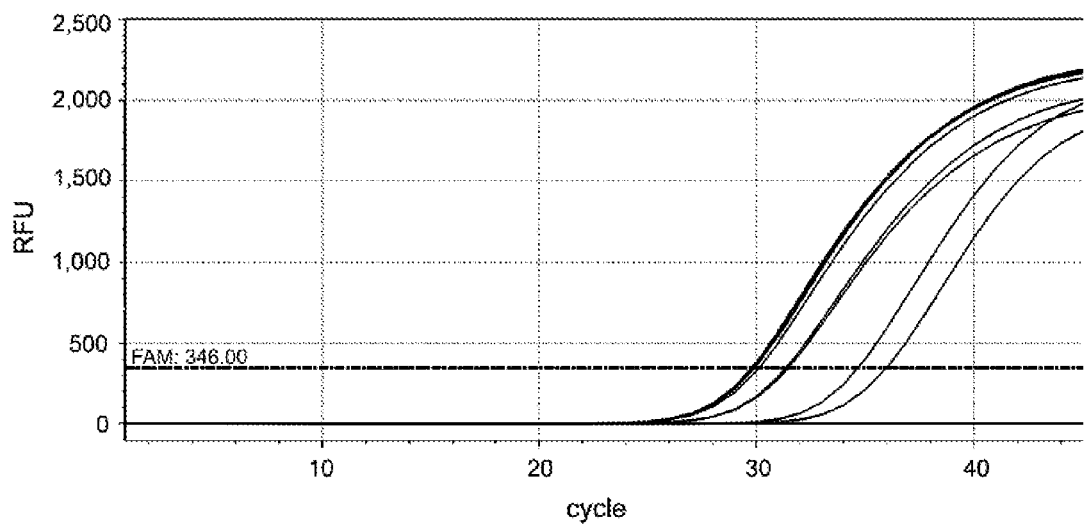
FIG. 7 shows a compatibility test of traditional PBS buffer and lysis buffer mixed at different ratios.
Figure 8:
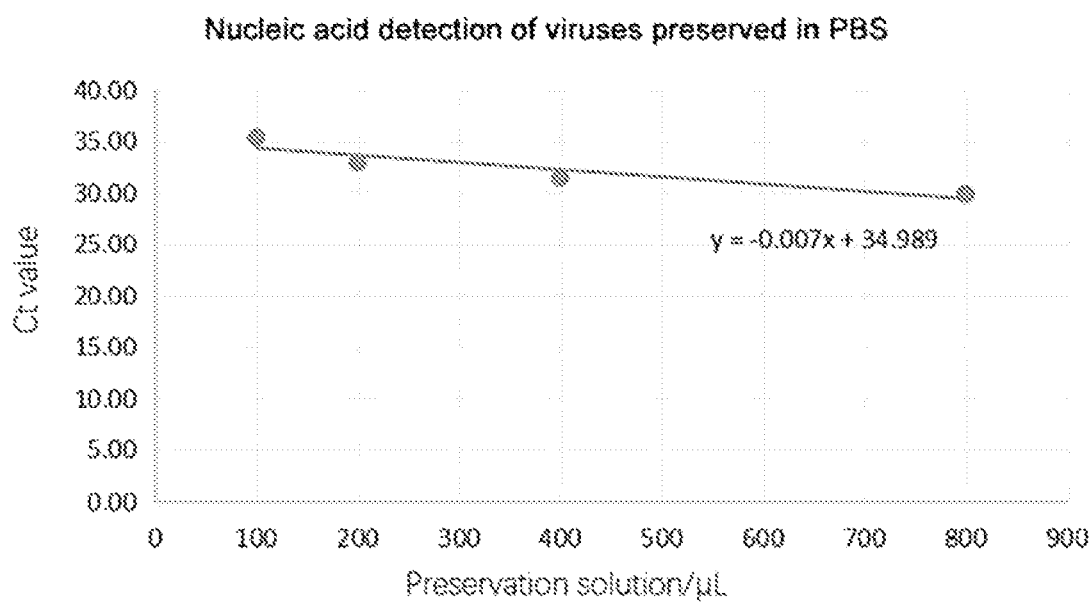
FIG. 8 shows a change trend of cycle threshold (Ct) value during the compatibility test of the traditional PBS buffer and lysis buffer mixed at different ratios.

FIG. 5, FIG. 7, and Table 7 showed that, the Ct values measured during nucleic acid extraction at the presence of the preservation solution B and the lysis buffer mixed at a ratio from low to high decreased successively, and meanwhile were all lower than the Ct values measured during nucleic acid extraction at the presence of the preservation solution C and the lysis buffer mixed at the same ratio. The change trends of the Ct values were shown in FIG. 6 and FIG. 8. As can be seen from FIG. 6 and FIG. 8, when the virus preservation solution of the present invention was used, the change trend of the Ct values is more obvious than that when the PBS was used, indicating that the virus preservation solution of the present invention can be mixed with the lysis buffer at different ratios and is well compatible with the lysis buffer.

Test 4. Test of Virus Preservation Solution Mixed with Lysis Buffers Having Different Formulations at Different Ratios Preservation solution D: 10 μL of pseudoviruses ($1\times10^5$ copies/ml) and a nasopharyngeal swab sample were added together into 3 mL of virus preservation solution and placed at room temperature (25° C.) for 1 h. Three different magnetic bead-based viral nucleic acid extraction kits (Dongsheng V4002, GenFine FM502T5-01, and Vazyme RM101) were respectively used for automated nucleic acid extraction. The preservation solution and lysis buffer were mixed according to the ratio in Table 8.

TABLE 8

Volume ratio of mixed preservation solution and lysis buffer

| Preservation solution/lysis buffer | Preservation solution D (μL) | Lysis buffer (μL) |
|---|---|---|
| 1/7 | 100 | 700 |
| 1/3 | 200 | 600 |
| 1/1 | 400 | 400 |
| 8/0 | 800 | 0 |

20 μL of magnetic beads, 2 μL of carrier RNA, and 20 μL of proteinase K were added to the above mixed solutions, respectively, followed by mixing well and transferring to 96-well deep-well plates. The subsequent extraction operation was the same as that in test 1. The nucleic acid samples were obtained after extraction. The nucleic acid detection procedure was the same as that in test 1. The nucleic acid testing results were shown in FIGS. 9, 11 and 13, and the corresponding Ct values were shown in Table 9.

TABLE 9

Ct values of three test groups

| Sample | Ct values | Average Ct value |
|---|---|---|
| Dongsheng 1/7 | 28.30 | 28.36 |
|  | 28.41 |  |
| Dongsheng 1/3 | 27.02 | 27.09 |
|  | 27.15 |  |
| Dongsheng 1/1 | 26.11 | 26.16 |
|  | 26.21 |  |
| Dongsheng 8/0 | 25.02 | 25.11 |
|  | 25.19 |  |
| GenFine 1/7 | 30.33 | 30.45 |
|  | 30.57 |  |
| GenFine 1/3 | 28.43 | 28.45 |
|  | 28.47 |  |
| GenFine 1/1 | 27.23 | 27.26 |
|  | 27.29 |  |
| GenFine 8/0 | 25.99 | 26.00 |
|  | 26.00 |  |
| Vazyme 1/7 | 28.96 | 28.84 |
|  | 28.71 |  |
| Vazyme 1/3 | 27.73 | 27.76 |
|  | 27.78 |  |
| Vazyme 1/1 | 26.75 | 26.78 |
|  | 26.80 |  |
| Vazyme 8/0 | 25.24 | 25.36 |
|  | 25.48 |  |

Figure 9:
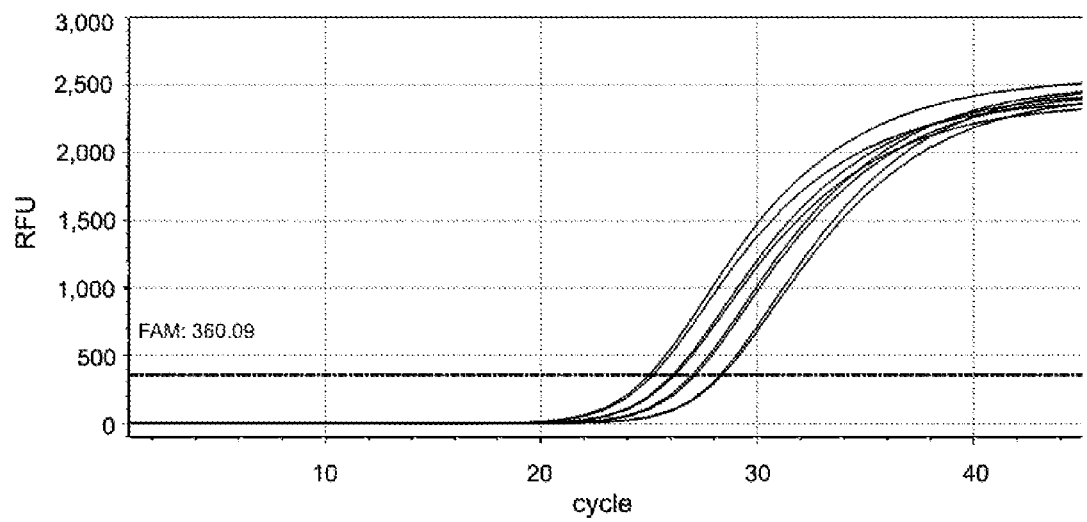
FIG. 9 shows a compatibility test of the virus preservation solution of Embodiment 1 and the nucleic acid extraction reagent from Dongsheng Biotech Co., Ltd.
Figure 10:
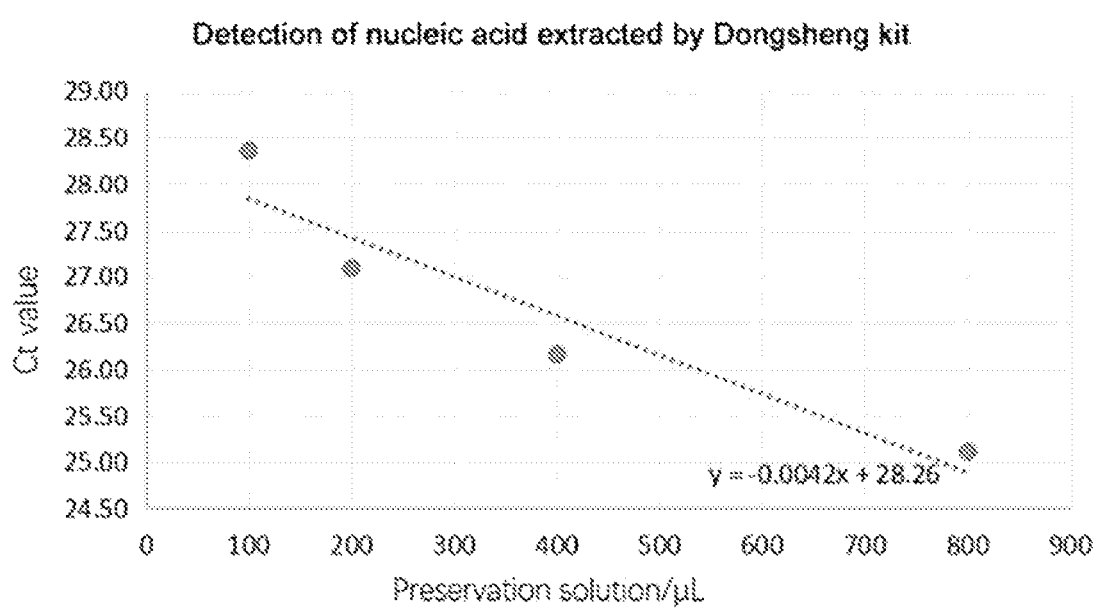
FIG. 10 shows a change trend of cycle threshold (Ct) value during the compatibility test of the virus preservation solution of Embodiment 1 and the nucleic acid extraction reagent from Dongsheng Biotech Co., Ltd.
Figure 11:
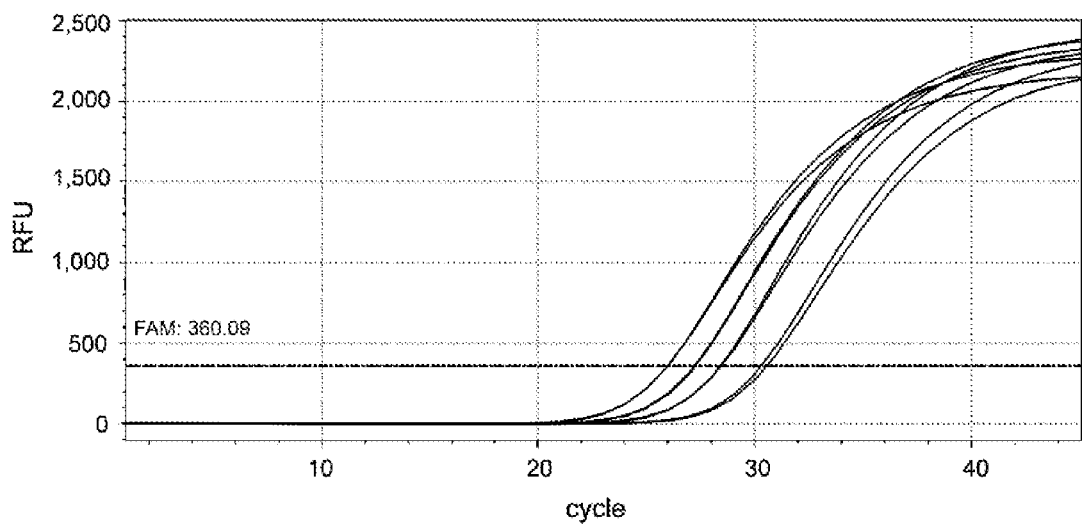
FIG. 11 shows a compatibility test of the virus preservation solution of Embodiment 1 and the nucleic acid extraction reagent from GENFINE BIOTECH (BEIJING) CO., LTD.
Figure 12:
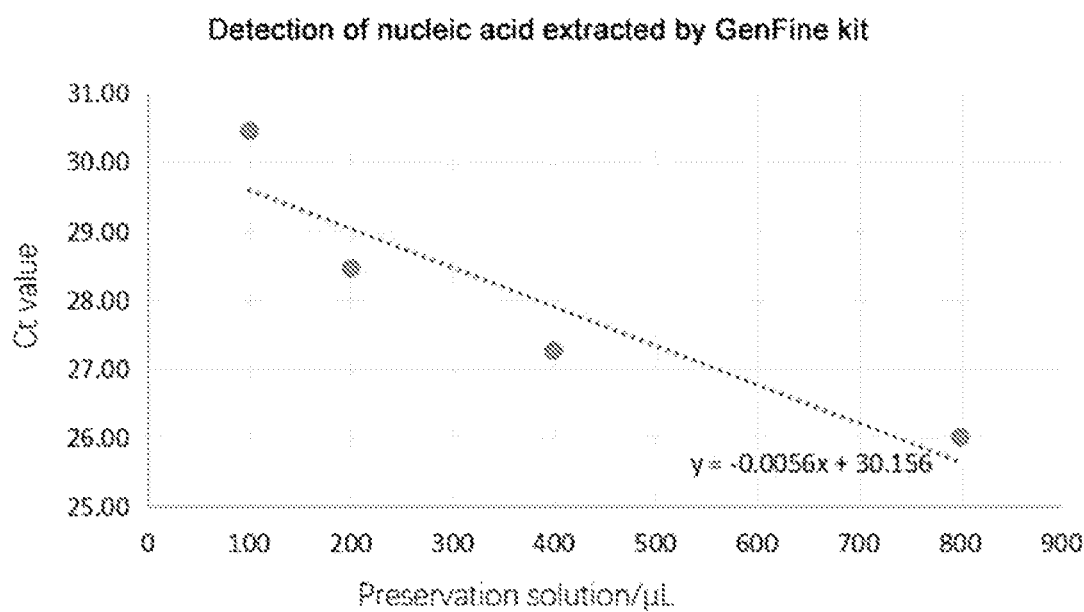
FIG. 12 shows a change trend of cycle threshold (Ct) value during the compatibility test of the virus preservation solution of Embodiment 1 and the nucleic acid extraction reagent from GENFINE BIOTECH (BEIJING) CO., LTD.
Figure 13:
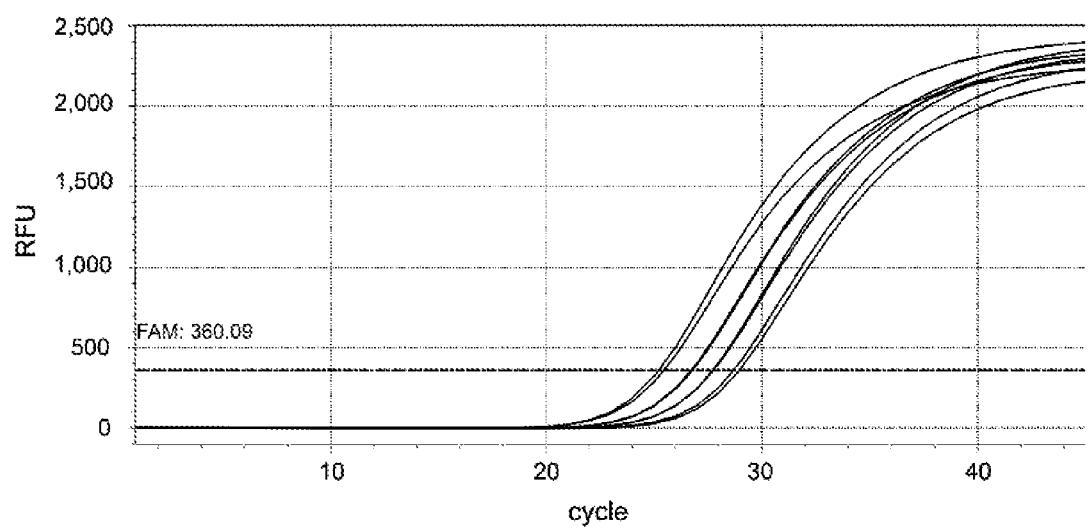
FIG. 13 shows a compatibility test of the virus preservation solution of Embodiment 1 and the nucleic acid extraction reagent from Vazyme Biotech Co., Ltd.
Figure 14:
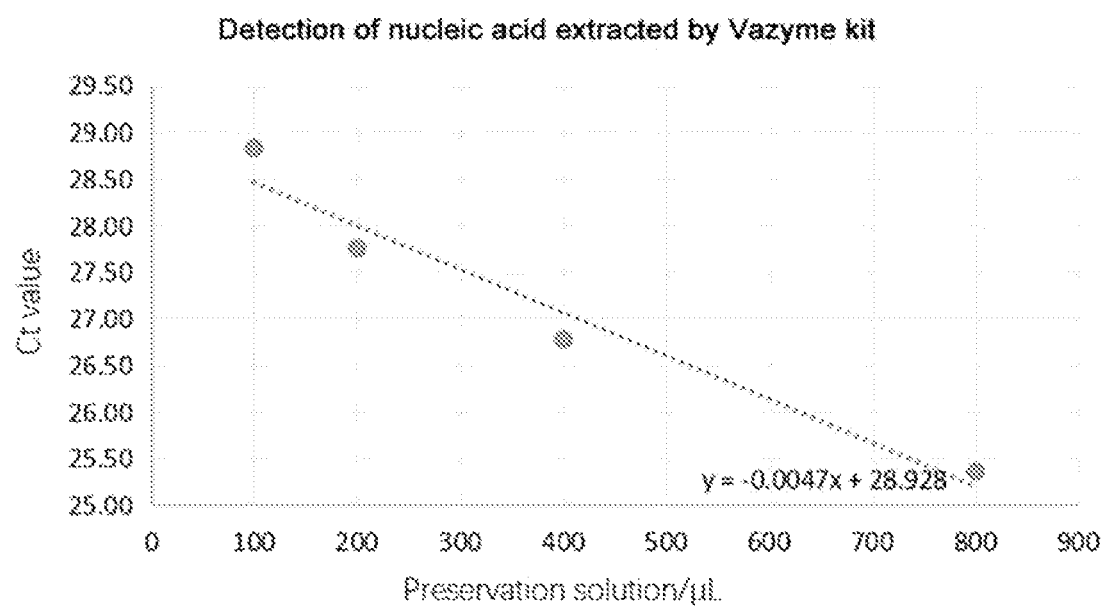
FIG. 14 shows a change trend of cycle threshold (Ct) value during the compatibility test of the virus preservation solution of Embodiment 1 and the nucleic acid extraction reagent from Vazyme Biotech Co., Ltd.

As can be seen from FIGS. 9, 11, 13 and Table 9, the three magnetic bead-based viral nucleic acid extraction kits were respectively used to extract nucleic acids from samples gradiently, the obtained viral RNA was detected, and the detection results were all valid. As shown in FIGS. 10, 12 and 14, the corresponding Ct values had the same change trend. The higher the ratio at which the sample was mixed with the lysis buffer is, the smaller the Ct value is, indicating that the virus preservation solution of the present invention can be well compatible with lysis buffers having different formulations, and more nucleic acids can be obtained by replacing part or all the lysis buffer with the virus preservation solution.

Test 5. Test of Virus Preservation Solution Comparing to Virus Preservation Solutions of Other Bands The virus preservation solution of Embodiment 1 was prepared and compared with the virus preservation solution (DOUBANG, Biocomma).

10 μL of pseudoviruses ($1\times10^4$ copies/mL) and a nasopharyngeal swab sample were added together into 3 mL of the virus preservation solution and placed at room temperature (25° C.) for 2 h. 100 μL, 200 μL, 400 μL and 800 μL of the sample-containing virus preservation solution were taken for nucleic acid extraction.

The nucleic acid extraction and detection procedure were the same as those in test 1 (Stability test of virus samples preserved in virus preservation solution).

Figure 15:
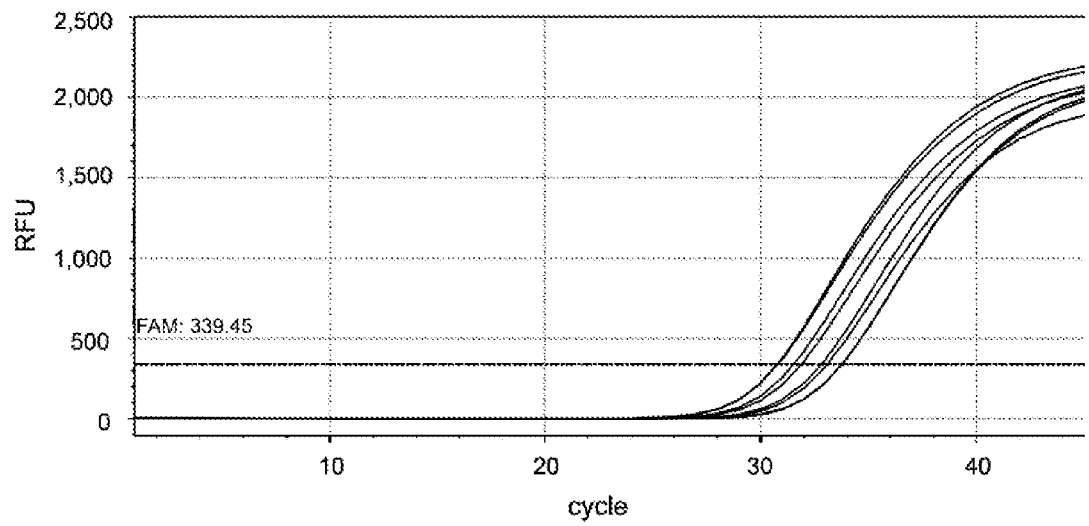
FIG. 15 shows a change trend of cycle threshold (Ct) value of the virus preservation solution from Dongsheng Biotech Co., Ltd. in Embodiment 1.
Figure 16:
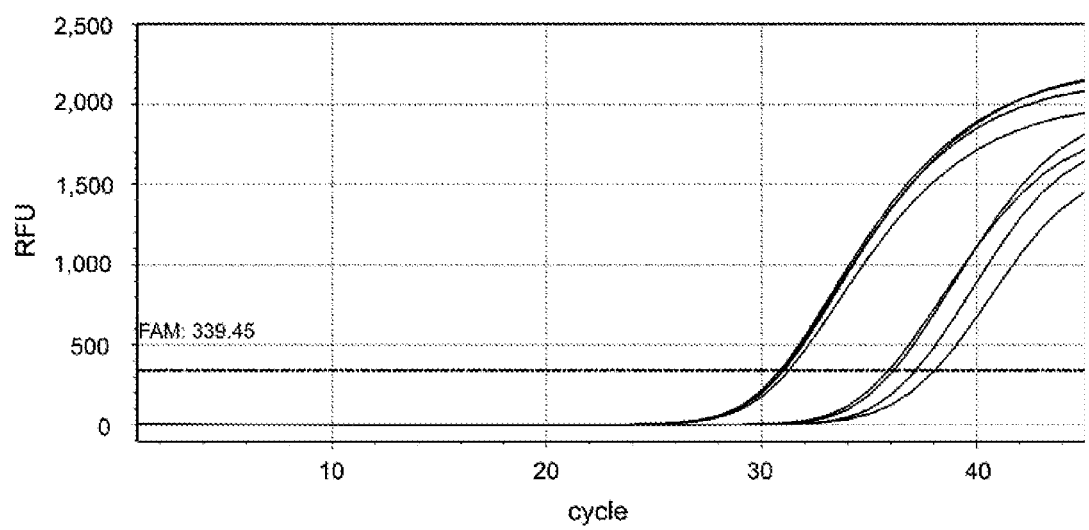
FIG. 16 shows a change trend of cycle threshold (Ct) value of the virus preservation solution from DOUBANG, Biocomma Inc.

The nucleic acid testing results were shown in FIG. 15 and FIG. 16, and the corresponding Ct values were shown in Table 10.

TABLE 10

| Sample | Ct values | Average Ct value |
| --- | --- | --- |
| Virus preservation solution of Embodiment 1 100 μL | 33.79<br>33.77 | 33.78 |
| Virus preservation solution of Embodiment 1 200 μL | 32.82<br>33.09 | 32.96 |
| Virus preservation solution of Embodiment 1 400 μL | 31.54<br>31.89 | 31.72 |
| Virus preservation solution of Embodiment 1 800 μL | 30.79<br>30.83 | 30.81 |
| DOUBANG 100 μL | 38.06<br>37.17 | 37.62 |
| DOUBANG 200 μL | 36.14<br>35.9 | 36.02 |
| DOUBANG 400 μL | 30.86<br>30.94 | 30.90 |
| DOUBANG 800 μL | 31.05<br>31.27 | 31.16 |
| No template control (NTC) | — | — |

The results showed that the virus preservation solutions (Embodiment 1) had good extraction efficiency when the amounts thereof used changed gradiently, which presented in a certain gradient relationship. While the extraction efficiency of the virus preservation solutions (DOUBANG, Biocomma) did not have good correlation with the gradient change of the amounts of virus preservation solutions used, and had poor extraction efficiency at a low sample concentration.

Test 6. Test of Virus Preservation Solution Containing Gradient Concentrations of Guanidine Hydrochloride The virus preservation solution of Embodiment 1 was prepared, in which the concentration of the guanidine hydrochloride was 5 mol/L. The virus preservation solutions of control group respectively contained 1 mol/L and 3 mol/L of guanidine hydrochloride.

10 μL of pseudoviruses ($1\times10^4$ copies/mL) and a nasopharyngeal swab sample were added together into 3 mL of virus preservation solution and placed at room temperature (25° C.) for 2 h, and then 200 μL of the sample-containing virus preservation solution was taken for nucleic acid extraction.

The nucleic acid extraction and detection procedure were the same as those in Test 1 (Stability test of virus samples preserved in virus preservation solution).

Figure 17:
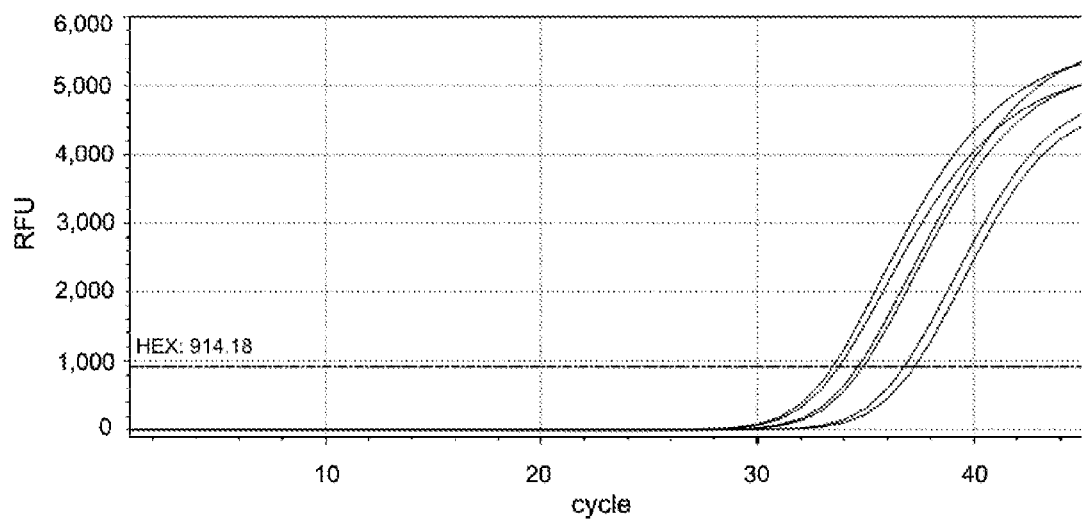
FIG. 17 shows a change trend of cycle threshold (Ct) value during a test of the virus preservation solution of Embodiment 1 having gradient concentrations of guanidine hydrochloride.
Figure 18:
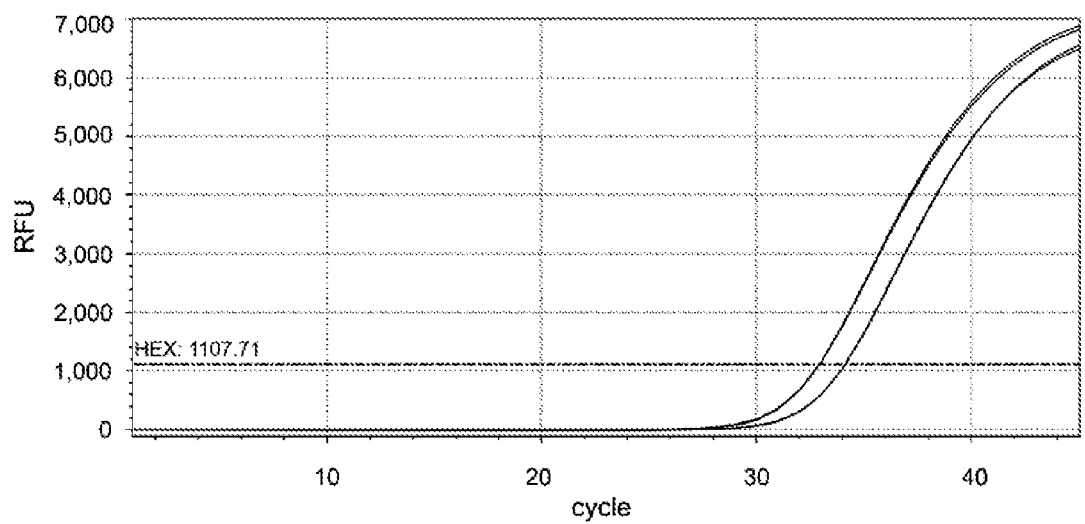
FIG. 18 shows a change trend of cycle threshold (Ct) value during a test of the virus preservation solution of Embodiment 3 with or without isopropanol.

The nucleic acid testing results were shown in FIG. 17, and the corresponding Ct values were shown in Table 11.

TABLE 11

| Final concentration of guanidine hydrochloride | Ct values | Average Ct value |
| --- | --- | --- |
| 1 mol/L | 36.77<br>37.26 | 37.02 |
| 3 mol/L | 34.89<br>34.65 | 34.77 |
| 5 mol/L | 33.76<br>33.49 | 33.63 |

The results showed that the preservation solutions having 3 mol/L and 5 mol/L of guanidine hydrochloride had good lysis effect, thus obtaining high nucleic acid extraction efficiency, while the preservation solution having 1 mol/L of guanidine hydrochloride had much lower nucleic acid extraction efficiency, indicating that the preservation solution having 1 mol/L of guanidine hydrochloride had poor lysis effect.

Test 7. Test of Virus Preservation Solution with or without Isopropanol

The virus preservation solution of Embodiment 3 was prepared, in which isopropanol had a volume percentage of 10% (V/V). The virus preservation solution of control group contained isopropanol at a volume percentage of 0% (V/V).

10 μL of pseudoviruses ($1\times10^4$ copies/mL) and a nasopharyngeal swab sample were added together into 3 mL of virus preservation solution and placed at room temperature (25° C.) for 2 h, and then 200 μL of the sample-containing virus preservation solution was taken for nucleic acid extraction.

The nucleic acid extraction and detection procedure were the same as those in Test 1 (Stability test of virus samples preserved in virus preservation solution).

TABLE 12

| Final concertation of isopropanol (V/V) | Ct values | Average Ct value |
| --- | --- | --- |
| 0% | 34.13<br>34.12 | 34.13 |
| 10% | 32.92<br>32.94 | 32.93 |

The results showed that the preservation solution containing isopropanol at the final concentration of 10% had a good lysis effect, so as to obtain a higher nucleic acid extraction efficiency, while the preservation solution without isopropanol had a much lower nucleic acid extraction efficiency, indicating that isopropanol was a very important component in the preservation solution.

In the description of this specification, the reference term "an embodiment", "some embodiments", "examples", "specific examples", or "some examples" etc. means that the specific feature, structure, material or characteristic described in conjunction with the embodiment or example is included in at least one embodiment or example of the present invention. The exemplary expressions of such terms in this specification do not need to refer to the same embodiments or examples. Furthermore, the specific feature, structure, material or characteristic described may be combined in an appropriate manner in any one or more embodiments or examples. In addition, without contradicting each other, a skilled person in the field may combine the different embodiments or examples described in this specification and the features of the different embodiments or examples.

Although embodiments of the present invention have been shown and described above, it is understood that the above embodiments are exemplary and should not be construed as limiting the present invention. Variations, modifications, replacements and transformation can be made to the above embodiments by those of ordinary skills in the art within the scope of the present invention.

What is claimed is:

1. A virus lysis and nucleic acid preservation solution, comprising the following components:
   isopropanol or ethyl alcohol,
   guanidine hydrochloride,
   tris (hydroxymethyl) aminomethane hydrochloride,
   ethylenediaminetetraacetic acid,
   proteinase K and
   magnetic beads, wherein a concentration of the guanidine hydrochloride is 5-6 mol/L, a concentration of the tris (hydroxymethyl) aminomethane hydrochloride is 10-100 mmol/L, a concentration of the ethylenediaminetetraacetic acid is 2-5 mmol/L, and a volume percentage of the isopropanol or ethyl alcohol is 5%-40%, wherein the magnetic beads are hydroxyl magnetic beads, and wherein the guanidine hydrochloride in the virus lysis and nucleic acid preservation solution does not cause proteinase K inactivation or aggregation of the magnetic beads.

2. The virus lysis and nucleic acid preservation solution according to claim 1, wherein in the virus lysis and nucleic acid preservation solution, the concentration of the guanidine hydrochloride is 5 mol/L, the concentration of the tris (hydroxymethyl) aminomethane hydrochloride is 50-80 mmol/L, and the concentration of the ethylenediaminetetraacetic acid is 2.5-4 mmol/L, and the volume percentage of the isopropanol or ethanol is 10%-30%.

3. The virus lysis and nucleic acid preservation solution according to claim 1, wherein a pH of the virus lysis and nucleic acid preservation solution is 6-9.

4. The virus lysis and nucleic acid preservation solution according to claim 3, wherein a pH of the virus lysis and nucleic acid preservation solution is 7-8.

5. The virus lysis and nucleic acid preservation solution according to claim 1, wherein the virus lysis and nucleic acid preservation solution is prepared with sterile water as a solvent.

6. A kit, comprising the virus lysis and nucleic acid preservation solution according to claim 1, wherein the kit is configured for a virus preservation and/or a nucleic acid extraction.

7. A method for preserving viral nucleic acid comprising a step of adding the solution according to claim 1 to a sample containing a virus.

8. The virus lysis and nucleic acid preservation solution according to claim 2, wherein a pH of the virus lysis and nucleic acid preservation solution is 6-9.

9. The virus lysis and nucleic acid preservation solution according to claim 2, wherein the virus lysis and nucleic acid preservation solution is prepared with sterile water as a solvent.

10. The kit according to claim 6, wherein in the virus lysis and nucleic acid preservation solution, the concentration of the guanidine hydrochloride is 5 mol/L, the concentration of the tris (hydroxymethyl) aminomethane hydrochloride is 50-80 mmol/L, the concentration of the ethylenediaminetetraacetic acid is 2.5-4 mmol/L, and the volume percentage of the isopropanol or ethanol is 10%-30%.

11. The kit according to claim 6, wherein a pH of the virus lysis and nucleic acid preservation solution is 6-9.

12. The kit according to claim 11, wherein a pH of the virus lysis and nucleic acid preservation solution is 7-8.

13. The kit according to claim 6, wherein the virus lysis and nucleic acid preservation solution is prepared with sterile water as a solvent.

\* \* \* \* \*

SEQUENCE LISTING

<160> NUMBER OF SEQ ID NOS: 6

<210> SEQ ID NO 1
<211> LENGTH: 21
<212> TYPE: DNA
<213> ORGANISM: Artificial Sequence
<220> FEATURE:
<223> OTHER INFORMATION: The sequence is synthesized

<400> SEQUENCE: 1
ccctgtgggt tttacactta a                                             21

<210> SEQ ID NO 2
<211> LENGTH: 19
<212> TYPE: DNA
<213> ORGANISM: Artificial Sequence
<220> FEATURE:
<223> OTHER INFORMATION: The sequence is synthesized

<400> SEQUENCE: 2
acgattgtgc atcagctga                                                19

<210> SEQ ID NO 3
<211> LENGTH: 28
<212> TYPE: DNA
<213> ORGANISM: Artificial Sequence
<220> FEATURE:
<223> OTHER INFORMATION: The sequence is synthesized
<220> FEATURE:
<221> NAME/KEY: misc_feature
<222> LOCATION: (1)..(21)
<223> OTHER INFORMATION: The sequence is a fluorescence probe with FAM
      at the 5' end and BHQ1 at the 3' end

<400> SEQUENCE: 3
ccgtctgcgg tatgtggaaa ggttatgg                                      28

<210> SEQ ID NO 4
<211> LENGTH: 22
<212> TYPE: DNA
<213> ORGANISM: Artificial Sequence
<220> FEATURE:
<223> OTHER INFORMATION: The sequence is synthesized

<400> SEQUENCE: 4
ggggaacttc tcctgctaga at                                            22

<210> SEQ ID NO 5
<211> LENGTH: 22
<212> TYPE: DNA
<213> ORGANISM: Artificial Sequence
<220> FEATURE:
<223> OTHER INFORMATION: The sequence is synthesized

<400> SEQUENCE: 5
cagacatttt gctctcaagc tg                                            22

<210> SEQ ID NO 6
<211> LENGTH: 19
<212> TYPE: DNA
<213> ORGANISM: Artificial Sequence
<220> FEATURE:
<223> OTHER INFORMATION: The sequence is synthesized
<220> FEATURE:
<221> NAME/KEY: misc_feature
<222> LOCATION: (1)..(19)
<223> OTHER INFORMATION: The sequence is a fluorescence probe with HEX
      at the 5' end and TAMRA at the 3' end

```
<400> SEQUENCE: 6
ttgctgctgc ttgacagat                                              19
```